(12) United States Patent
Haunschild et al.

(10) Patent No.: US 9,435,740 B2
(45) Date of Patent: Sep. 6, 2016

(54) METHOD FOR MEASURING A SEMICONDUCTOR STRUCTURE, WHICH IS A SOLAR CELL OR A PRECURSOR OF A SOLAR CELL

(75) Inventors: Jonas Haunschild, Freiburg (DE); Stefan Rein, Denzlingen (DE); Markus Glatthaar, Freiburg (DE)

(73) Assignee: FRAUNHOFER-GESELLSCHAFT ZUR FORDERUNG DER ANGEWANDTEN FORSCHUNG E.V., Munich (DE)

( * ) Notice: Subject to any disclaimer, the term of this patent is extended or adjusted under 35 U.S.C. 154(b) by 924 days.

(21) Appl. No.: 13/393,320

(22) PCT Filed: Aug. 16, 2010

(86) PCT No.: PCT/EP2010/005018
§ 371 (c)(1),
(2), (4) Date: Apr. 25, 2012

(87) PCT Pub. No.: WO2011/023312
PCT Pub. Date: Mar. 3, 2011

(65) Prior Publication Data
US 2012/0203494 A1    Aug. 9, 2012

(30) Foreign Application Priority Data
Aug. 31, 2009    (DE) .................. 10 2009 039 399

(51) Int. Cl.
*G01N 21/64*    (2006.01)
*G01N 21/95*    (2006.01)
(Continued)

(52) U.S. Cl.
CPC ...... *G01N 21/6489* (2013.01); *G01N 21/9501* (2013.01); *H02S 50/10* (2014.12); *G01N 21/66* (2013.01); *G01N 2015/1479* (2013.01); *G03F 7/2008* (2013.01); *G06F 17/00* (2013.01)

(58) Field of Classification Search
CPC ............ G01N 21/6489; G01N 21/66; G01N 21/9501; G01N 21/95623; G01N 2021/9544; G01N 21/95607; G01N 2015/1479; G03F 7/2008; G06F 17/00
USPC ........................................................ 702/117
See application file for complete search history.

(56) References Cited

U.S. PATENT DOCUMENTS

2009/0206287 A1    8/2009  Trupke et al.

FOREIGN PATENT DOCUMENTS

DE    102007045830    4/2009
DE    202009017763    6/2010
(Continued)

OTHER PUBLICATIONS

Trupke, T. et al., "Spatially Resolved Series Resistance of Silicon Solar Cells Obtained from Luminescence Imaging", Applied Physics Letters, AIP, American Institute of Physics, Melville, NY, Bd. 90, Nr. 9, Feb. 28, 2007.

(Continued)

*Primary Examiner* — Toan Le
*Assistant Examiner* — Lynda Dinh
(74) *Attorney, Agent, or Firm* — Volpe and Koenig, P.C.

(57) ABSTRACT

A method is provided for measuring a semiconductor structure, which allows the spatially resolved determination of dark saturation current and/or series resistance and/or resistance of the emitter layer of the semiconductor structure via luminescence measurement, without restrictions being given such that one of the parameters must be known in advance or spatially consistent.

15 Claims, 1 Drawing Sheet

(51) Int. Cl.
*H02S 50/10* (2014.01)
*G01N 21/66* (2006.01)
*G06F 17/00* (2006.01)
*G03F 7/20* (2006.01)
*G01N 15/14* (2006.01)

(56) References Cited

FOREIGN PATENT DOCUMENTS

| EP | 1758178 | 2/2007 |
|---|---|---|
| WO | 2008095467 | 8/2008 |
| WO | 2009103566 | 8/2009 |

OTHER PUBLICATIONS

Glatthaar, Markus, et al., "Spatially Resolved Determination of the Dark Saturation Current of Silicon Solar Cells from Electroluminescence Images", Journal of Applied Physics, American Institute of Physics, New York, NY, Bd. 105, Jan. 1, 2009.

Psych et al., "A Review and Comparison of Different Methods to Determine the Series Resistance of Solar Cells", Solar Energy Materials and Solar Cells, Elsevier Science Publishers, Amsterdam, Netherlands, Bd. 91, Nr. 18, Aug. 30, 2007, pp. 1698-1706.

Wurfel, P. et al., "Diffusion Lengths of Silicon Solar Cells from Luminescence Images", Journal of Applied Physics, American Institute of Physics, New York, NY, Bd. 101, Jan. 1, 2007.

Kampwerth, H., et al., "Advanced Luminescence Based Effective Series Resistance Imaging of Silicon Solar Cells", Applied Physics Letters, AIP, American Institute of Physics, Melville, NY, Bd. 93, Nr. 20, Nov. 18, 2008.

Michl, B., et al., "Application of Luminescence Imaging Based Series Resistance Measurements Methods in an Industrial Environment", Proceedings of the 23rd European Photovoltaic Solar Energy Conference and Exhibition, Valencia, Spain, Sep. 1, 2008, pp. 1-6.

Ramspeck, K., et al., "Recombination Current and Series Resistance Imaging of Solar Cells by Combined Luminescence and Lock-In Thermography", Applied Physics Letters, AIP, American Institute of Physics, Melville, NY, Bd. 90, Nr. 15, Apr. 9, 2007.

A { creating luminescence radiation in the semiconductor structure and spatially resolved measurements of the luminescence radiation emitted by the semiconductor structure, with a first measurement being performed at a first measuring condition a and depending at least on the measurements yielded from the first measurement, a first spatially resolved, voltage-calibrated image $V_a(x_i)$ being determined for a multitude of spatial points $x_i$ of the solar cell from the measurements yielded in step A, in step A additionally at least a second measurement is performed at a second measurement condition b different from the first measurement condition a and, depending at least on the measurements yielded from the second measurement, a second spatially resolved, voltage calibrated image Vb(xi) is determined for the multitude of spatial points xi from the measurements yielded in step A such that in step A in the two measurements
- the luminescence radiation is essentially created by a planar impingement of the semiconductor structure with an excitation radiation,
- the measuring conditions (a, b) of the first and second measurement are different with regards to the intensities and/or spectral compositions of the excitation radiation and/or a predetermined external voltage Vext, by which the semiconductor structure is impinged via electric contacts additionally for each measuring condition (a, b) a voltage-independent, spatially independent short-circuit current density ($j_{P,a}$, $j_{P,b}$) of the current flowing under the respective measuring conditions with given short-circuit conditions is predetermined and/or measured

B { determining spatially resolved features of the semiconductor structure with regards to the spatially resolved dark saturation current $j_0(x_i)$ and/or the spatially resolved resistance of the emitter layer $\rho(x_i)$ and/or the spatially resolved local series resistance $R_s(x_i)$ for the multitude of spatial points $x_i$ dependent at least on the first voltage image $V_a(x_i)$ determined in step A in step B the determination of the spatially resolved, electric features occurs at each spatial location $x_i$ is dependent on at least the short-circuit current densities ($j_{P,a}$, $j_{P,b}$) and a voltage-dependent, spatially dependent dark current density ($j_{D,a}(x_i)$, $j_{D,b}(x_i)$) for each measurement condition occurs, with the dark current densities ($j_{D,a}(x_i)$, $j_{D,b}(x_i)$) at least being dependent on the voltage-independent dark saturation current density ($j_0,x_i$) and the two voltages ($V_a(x_i)$, $V_b(x_i)$) resulting from the respective voltage images for the location $x_i$.

METHOD FOR MEASURING A SEMICONDUCTOR STRUCTURE, WHICH IS A SOLAR CELL OR A PRECURSOR OF A SOLAR CELL

BACKGROUND

The invention relates to a method for measuring a semiconductor structure, with the semiconductor structure comprising an emitter and a base, and being a solar cell or a precursor of a solar cell.

In semiconductor structures for example based on an indirect semiconductor, such as silicon, it is known to obtain information, concerning the physical features of the semiconductor structure based on a luminescence radiation created in the semiconductor structure. In particular, measurements of the luminescence radiation are used to determine spatially resolved electric parameters in a semiconductor structure, which is a solar cell or a precursor of a solar cell and comprises at least an emitter and a base.

Here, it is known to determine the diffusion length of the semiconductor material from the measurement of the luminescence radiation, such as described in Würfel, P. et al., "*Diffusions lengths of silicon cells from luminescence images*", Journal of Applied Physics, 2007, 101 (123110): p. 1-10.

In order to characterize solar cells, particularly to control the quality of industrially produced solar cells, it is desired to determine additional spatially resolved electric parameters, particularly the dark saturation current, the resistance of the emitter layer, and the local series resistance.

In luminescence radiation essentially created by impinging the semiconductor structure with an excitation voltage (so-called "electro-luminescence radiation") it is known to determine the dark saturation current from two spatially resolved measurements of the electro-luminescence under different measuring conditions. Such a method is described in M. Glatthaar, J. Giesecke, M. Kasemann, J. Haunschild, M. The, W. Warta, and S. Rein, Journal of Applied Physics 105, 113110/1-5 (2009). However, this measuring method is disadvantageous in that, for example, the resistance of the emitter layer must be known and furthermore it must be spatially constant. In particular in industrially produced solar cells the resistance of the emitter layer frequently varies over the surface of the solar cell so that the above-mentioned conditions are not fulfilled. Furthermore, the method requires an extended measuring period so that it cannot be used in-line within a production process.

SUMMARY

Therefore the objective of the invention is to provide a method for measuring a semiconductor structure, which allows the spatially resolved determination of dark saturation current and/or series resistance and/or resistance of the emitter layer of the semiconductor structure via luminescence measurement, without restrictions being given such that one of the parameters must be known in advance or spatially consistent.

This objective is attained in a method according to the invention.

The semiconductor structure is a solar cell or a precursor of a solar cell. It is essential that the semiconductor structure already comprises an emitter and a base.

The method according to the invention comprises the following processing steps.

In a step A a luminescence radiation is created in the semiconductor structure and a spatially resolved measurement occurs of the luminescence radiation emitted by the semiconductor structure. Typically solar cells are planar formations, i.e. the front and the rear of the solar cell comprise an essentially larger length and width in reference to the thickness of the solar cell. In the following, the word "spatially resolved" relates therefore always to several spatial locations parallel in reference to the front and rear side of the solar cell, however not to any arrangement of several local points with regards to the depth of the solar cell, i.e. along a line perpendicular in reference to the front or rear side.

In step A at least one spatially resolved measurements of the luminescence radiation occurs at a first measuring condition a.

Furthermore, in step A at least one first spatially resolved, voltage-calibrated image is determined from the measurements yielded in step A. The term "voltage-calibrated image" relates here to a spatially resolved, voltage calibrated image $V_a(x_i)$, i.e. a multitude of voltage values, which are allocated to respective spatial points $x_i$ of the solar cell. Here, the voltage values describe the voltage locally applied under the respective measuring conditions at the spatial point $x_i$ at a semiconductor structure and/or the pn-junction of the local voltage drop forming between the emitter and the base. Thus, in step B a first spatially resolving voltage image $V_a(x_i)$ is determined according to the first measurement conditions.

In a step B, the spatially resolved features of the semiconductor structure are determined regarding the spatially resolving dark saturation current $j_0(x_i)$ and/or the locally resolved resistance of the emitter layer $\rho(X_i)$ and/or the spatially resolved, local series resistance $R_s(x_i)$ for the plurality of spatial points xi, with the determination being dependent on the voltage-calibrated images determined in step A.

BRIEF DESCRIPTION OF THE DRAWING

FIG. 1 is a flow diagram depicting the method of the present invention.

BRIEF DESCRIPTION OF THE PREFERRED EMBODIMENTS

It is essential that in step A additionally at least one second measurement is performed under a second measuring condition b different from the first measuring condition a, and dependent on at least the measurements yielded from the second measuring a second spatially resolved, voltage calibrated image $V_b(x_i)$ is determined for a multitude of spatial points $x_i$ from the measurements yielded in step A. In both measurements in step A the luminescence radiation is essentially created by planar impingement of the semiconductor structure with an excitation radiation. Furthermore, the measurement conditions of the first and second measurement are different with regards to the intensities and/or spectral composition of the excitation radiation and/or regarding a predetermined external voltage $V_{ext}$, by which the semiconductor structure is impinged via electric contacts.

Furthermore, in addition to each measuring condition a voltage-independent, spatially independent short-circuit current density $j_{P,a/b}$ is predetermined and/or measured additionally. The short-circuit current density $j_{P,a/b}$ lists the area-standardized short-circuit current, which develops under the respective measuring conditions when short-circuit conditions are given (i.e. short-circuited electric contacts). When the measurement is performed at a precursor of a solar cell, which does not yet have any electric contacting structures, the predetermined short-circuit current densities are equivalent to those flowing after the completion of the solar cell under respective measuring conditions when short-circuit conditions exist between the electric contacts.

In the method according to the invention, in step B the determination of the spatially resolved electric features occurs at each spatial point xi dependent on at least the short circuit current densities $j_{P,a/b}$ and a voltage-dependent, spatially dependent dark current density $j_{D,a/b}(x_i)$. The dark current density $j_{D,a/b}(x_i)$ is here determined via a mathematic model, which is at least dependent on the voltage-independent dark saturation current density $j_0(x_i)$ and the two voltages $V_{a/b}(x_i)$ for the respective location xi resulting from the respective voltage-calibrated images.

The method according to the invention is based on the realization of the applicant that in the semiconductor structures to be measured at least two independent parameters may cause local changes in voltage, for example the spatial series resistance $R_s$ and the spatially resolved dark saturation current $j_0$ or the spatially resolved resistance of the emitter layer $\rho$ and the spatially resolved dark saturation current $j_0$. Due to the fact that the spatially resolved, voltage dependent current density of the semiconductor structure can be approximated in luminescence measurements by adding the spatially independent, voltage independent short-circuit current density and the voltage-independent and spatially dependent dark current density in the method according to the invention, by the use of at least two spatially resolved, voltage calibrated images and the short circuit current flow density $j_{P,a/b}$, the determination of both independent parameters is possible. However, this is only applicable if the luminescence radiation is essentially created via an excitation radiation, thus representing photoluminescence radiation (PL).

Therefore, contrary to methods of prior art, in the method according to the invention an additional information is used by predetermining and/or measuring the short-circuit current density $j_{P,a/b}$ and at least two voltage images. This results in the advantage that a determination of the dark saturation current density and/or the resistance of the emitter layer and/or the series resistance is possible, each in a spatially resolved manner, without any of these parameters (particularly the dark saturation current density) being required to be spatially independent and/or known.

Thus, by the methods according to the invention the possibilities for characterization in the analysis of a solar cell are essentially expanded via measurements of the photoluminescence radiation. Furthermore, the method according to the invention can be performed with short measurement durations so that it can be used in-line in a production process.

Preferably, in step B the determination of the spatially resolved, electric features at any spatial point $x_i$ occurs additionally dependent on an external voltage $V_{ext,a}$ with measuring conditions a and $V_{ext,b}$ with measuring conditions b. Here, in step A, in both measurements the semiconductor structure is electrically contacted and via the electric contacting the external voltage $V_{ext,a}$ is predetermined for the measuring condition a and $V_{ext,b}$ for the measuring condition b. Alternatively, for the voltage $V_{ext,a}$ the voltage of the spatial point is predetermined with the lowest voltage in the voltage image $V_a(x_i)$: $V_{ext,a}:=\text{Min}(V_a(x_i))$ for all spatial points $x_i$. Accordingly, $V_{ext,b}:=\text{Min}(V_b(x_i))$ is predetermined for all spatial points $x_i$ for the first external voltage under the measuring condition B. The second alternative is particularly beneficial when the measurement is performed in precursors of a solar cell, which does not yet have any electric contacts. Thus, in this second alternative the solar cell and/or the precursor of the solar cell are not electrically contacted and the values $V_{ext,a}$ and $V_{ext,b}$ are therefore determined, as shown above, from the minimal values of the respective voltage images. In this second alternative, therefore measurement conditions are given of open-clamp voltages.

The luminescence radiation is essentially created by a planar impingement of the semiconductor structure with an excitation radiation. This means, that the luminescence radiation represents a "photoluminescence radiation". Additionally, the semiconductor structure is preferably contacted electrically and an external voltage $V_{ext}$ is predetermined by the electric contacting. Although the luminescence radiation is essentially created by the impingement of the semiconductor structure with excitation radiation, in the method according to the invention additionally the condition of the solar cell is predetermined by electric contacting and presetting the external voltage, by which particularly the current flowing in the solar cell being defined, including via the electric contacting. This also includes the presetting of a voltage 0. In the method according to the invention, contrary to measurements of the electroluminescence radiation of prior art, no essential creation of luminescence radiation occurs, though, based on the creation of a current via an exterior external voltage, but the luminescence radiation is essentially created by the excitation radiation and the external voltage serves additionally to determine the measuring conditions.

The general measurement design, particularly the type and manner of the impingement of the semiconductor structure with excitation radiation and the measurement of the photoluminescence radiation as well as the contacting of the semiconductor structure to predetermine an external voltage $V_{ext}$ occurs preferably in a manner known per se. Particularly the measurement of the luminescence radiation via a camera, preferably a CCD-camera, is advantageous in a known manner.

Similarly, the determination of the first and the second spatially resolved, voltage-calibrated image preferably occurs in a manner known per se, such as described in T. Trupke, E. Pink, R. A. Bardos, and M. D. Abbott, Applied Physics Letters 90, 093506-1-3 (2007). In this case, several spatially resolved measurements of the luminescence radiation are necessary for the two spatially resolved, voltage calibrated images: According to T. Trupke, E. Pink, R. A. Bardos, and M. D. Abbott, Applied Physics Letters 90, 093506-1-3 (2007) a PL-image can be voltage-calibrated with the help of three additional PL-images: A short-circuit and an idle image with low illumination density, in which lateral voltage differences can be neglected, as well as a short-circuit image with the same illumination intensity as in the image to be calibrated. At the low intensity it can be assumed that the voltage $V_i$ in each image point xi is identical to the voltage $V_{ext}$ applied.

This way, the unknown parameter $C_{v,i}$ can be determined from the formula 0 with the thermal voltage $V_T$, because for $C_{b,i}$ the intensity of the short-circuit image is to be set for the respective illumination density:

$$I_i = C_{v,i} \exp(V_i/V_T) + C_{b,i} \qquad \text{(formula 0)}$$

For the image to be calibrated it therefore follows:

$$V_i = V_T \log\left(\frac{I_i - C_{b,i}}{C_{v,i}}\right)$$

Preferably, in step B the determination of the spatially resolved electric features occurs for each spatial point $x_i$ such that an equation system is solved, which for each of the two voltage images $V_a(x_i)$ and $V_b(x_i)$ shows respectively an equation ($G_a$ and $G_b$). Here, the equation $G_a$ shows at least the spatially resolved, voltage-independent local series resistance $R_s(x_i)$, the voltage $V_a(x_i)$, the external voltage $V_{ext,a}$, the short-circuit current density $j_{P,a}$, and the dark current density $j_{D,a}(x_i)$. Here, $V_{ext,a}$ represents the external voltage applied during the measurement condition a. Accordingly, the equation $G_b$ shows at least $R_s(x_i)$, $V_b(x_i)$, $V_{ext,b}$, $j_{P,b}$, and $j_{P,b}(x_i)$, with $V_{ext,b}$ representing the external voltage applied during the measurement condition b. Here, an equation system with two equations is given, in which $R_s(x_i)$ and $j_0(x_i)$ represent the unknowns, so that in a manner known per se a determination of one or both of these values occurs. Therefore, in this advantageous embodiment by simply applying mathematic methods known per se it is possible to solve equation systems for determining the above-mentioned parameters in order to characterize the solar cell.

Preferably, the equation $G_a$ shows the following structure $$R_s(x_i) = \frac{V_{ext,a} - V_a(x_i)}{j_{P,a} + j_{D,a}(x_i)}, \quad \text{(Formula 1a)}$$

and the equation $G_b$ is accordingly structured as follows:

$$R_s(x_i) = \frac{V_{ext,b} - V_b(x_i)}{j_{P,b} + j_{D,b}(x_i)}, \quad \text{(Formula 1b)}$$

Here, it is within the scope of the invention that by common equivalent reformulation the structure can be changed. It is essential that the equation system shows only $R_s(x_i)$ and $j_0(x_i)$ as the unknowns.

In another preferred embodiment, in step B the determination of the spatially resolved, electric features occurs for each spatial point $x_i$ such that an equation system is solved, which for each of the two voltage images $V_a(x_i)$ and $V_b(x_i)$ one equation $G_{a'}$ and $G_{b'}$ each is provided, with the equation $G_{a'}$ at least showing the spatially resolved, voltage independent resistance of the emitter layer $\rho(x_i)$, the voltage $V_a(x_i)$, the external voltage $V_{ext,a}$, the short-circuit current density $j_{P,a}$, and the dark current density $j_{D,a}(x_i)$. Accordingly, the equation $G_{b'}$ comprises at least $\rho(x_i)$, $V_b(x_i)$, $V_{ext,b}$, $j_{P,b}$, and $j_{P,b}(x_i)$.

Thus, in this advantageous embodiment an equation system is given with two equations, with in this case the resistance of the emitter layer $\rho(x_i)$ and the dark saturation current density $j_0(x_i)$ represent the two unknowns, so that based on the equation system one or both of these parameters are determined.

Preferably, here the equation $G_{a'}$ shows the following structure:

$$\nabla^2 V_a(x_i) = \rho(x_i)(j_{P,a} + j_{D,a}(x_i)) \quad \text{(Formula 2a)}$$

and accordingly the equation $G_{b'}$ shows the following structure:

$$\nabla^2 V_b(x_i) = \rho(x_i)(j_{P,b} + j_{D,b}(x_i)) \quad \text{(Formula 2b)}.$$

This equation is yielded by a combination of Ohm's law and the continuity equation. Preferably, a potential noise in the measuring data is reduced such that the dual spatial derivation of the voltage according to the Laplace-operator in the formulas 2a and 2b is replaced by the derivation of a quadratic polynomial, which is adjusted to the environment of the measuring point via a mathematical fitting method. This type of description of the dual derivation is known per se and for example described in M. Glatthaar, J. Giesecke, M. Kasemann, J. Haunschild, M. The, W. Warta, and S. Rein "*Spatially resolved determination of the dark saturation current of silicon solar cells from electroluminescence images*", Journal of Applied Physics 105, 113110 (2009). Alternatively, in order to calculate the Laplace image the Marr-Hildreth operator (Laplacian of Gaussian) can be applied for the image according to David Marr, Ellen Catherine Hildreth, Theory of Edge Detection. In Proceedings of the Royal Society of London, B 207, 1980, page 187, 217.

Preferably, in the method according to the invention additionally an implied open circuit voltage ($V_{impl,a}$ for measuring conditions a and $V_{impl,b}$ for measuring conditions b) is determined for each spatial point $x_i$ and for each of the measuring conditions a and b and furthermore the voltage calibrated images $V_a(x_i)$ and $V_b(x_i)$ are additionally determined based on the implied open circuit voltages.

Preferably, the implied open circuit voltages are determined as follows. Using inductive measurements for at least one spatial point under measurement condition a and for at least one spatial point under measurement condition b each the implied open circuit voltage is determined for said spatial point. The determination can occur for example in a known manner as described in QSSPC, R. A. Sinton and A. Cuevas, Applied Physics Letters 69, 2510-2 (1996). Due to the fact that for one spatial point now both under measuring condition a as well as under measuring condition b the open circuit voltage is known, for this spatial point the factor $C_{v,j}$ according to formula 0 can be calculated both for the measuring condition a and also for the measuring condition b. Due to the fact that this factor is spatially independent, here a voltage calibration occurs, and voltage-calibrated images $V_a(x_i)$ and $V_b(x_i)$ are given for both measuring conditions.

Preferably the measuring conditions a and b differ by the intensities of illumination, particularly it is advantageous to select for example an intensity of one sun for measuring conditions a and of two suns for measuring conditions b, with one sun=1000 W/m².

Preferably, in the method according to the invention the intensity of illumination and the spectrum of the excitation radiation between measuring condition a and measuring condition b are not changed in step A, while in measuring condition a an external voltage $V_{ext,a}$ being predetermined, which is different from a predetermined external voltage $V_{ext,b}$ in the measuring condition b.

This shows the advantage that a change of the external voltage can be realized considerably easier and more precise, compared with a defined change of the intensity or the spectrum of the excitation radiation. In another advantageous embodiment the measuring condition a is selected such that via the electric contacting a current flows ranging from 15% to 35%, preferably approximately 25% of the short-circuit current of the solar cell under standard conditions. Here, standard conditions represent the normal testing conditions applicable for the type of solar cell. For silicon solar cells for creating electricity from sunlight this usually amounts to a luminance intensity of one sun (1,000 W/m²) at a spectrum AM1.5. Furthermore, the measuring condition b is selected such that via the electric contacting a current flows ranging from 65% to 85%, preferably approximately 75% of the short-circuit current of the solar cell under standard conditions. This selection of the measuring conditions is advantageous in the parameters also being relevant for the standard operation of the solar cell. Additionally, only moderate heating of the cell occurs by the sun. At lower intensities the currents are lower and thus also the lateral voltage differences, from which the information is gathered.

The dark current density $j_{D,a/b}(xi)$ is preferably described via the one-diode models known per se for describing solar cells, particularly according to the formulas 3a and 3b:

$$j_{D,a}(x_i) = j_0(x_i) \exp(V_a(x_i)/V_T) \quad \text{(Formula 3a)}$$

$$j_{D,b}(x_i) = j_0(x_i) \exp(V_b(x_i)/V_T) \quad \text{(Formula 3b)}$$

In another preferred embodiment of the method according to the invention, in step A additionally another measurement occurs under measuring conditions c, which are different from the measuring conditions a and b, and in step B accordingly another voltage image $V_c(xi)$ is determined. Furthermore, the dark current density $j_{D,a/b/c}(xi)$ is additionally described based on another parameter and in step B the determination of the spatially resolved features of the semiconductor structure is performed depending on at least the three voltage images $V_{,a/b/c}(xi)$. Therefore, in this preferred embodiment a more precise description of the dark current density is possible by including another (unknown) parameter, with the information additionally required for the additional parameter being obtained by the third voltage image $V_c(xi)$. This way, a more precise description of the dark current density $j_{D,a/b/c}(xi)$ is possible, so that accordingly a more precise result is yielded of the parameter determined in step B.

Here, preferably the dark current density is additionally described by a voltage-independent spatial parallel resistance $R_p(xi)$, preferably according to the formulas 4a through 4c:

$$j_{D,a}(x_i) = j_0(x_i) \exp(V_a(x_i)/V_T) + V_a(x_i)/R_p(x_i), \quad \text{(Formula 4a)}$$

$$j_{D,b}(x_i) = j_0(x_i) \exp(V_b(x_i)/V_T) + V_b(x_i)/R_p(x_i), \quad \text{(Formula 4b)}$$

$$j_{D,c}(x_i) = j_0(x_i) \exp(V_c(x_i)/V_T) + V_c(x_i)/R_p(x_i), \quad \text{(Formula 4c)}.$$

In particular, it is advantageous in step A to perform additionally another measurement under a measuring condition d different from the measuring conditions a, b, and c, and in step B respectively to determine a fourth voltage image $V_d(xi)$ and to additionally describe the dark current density $j_{D,a/b/c/d}(xi)$ based on another parameter. Accordingly, in step B the determination of the spatially resolved features of the semiconductor structure occurs depending on at least the four voltage images $V_{a,b,c,d}(xi)$. Here, preferably the dark current density is described additionally by a second diode dependency according to the two-diode model known per se, using an additional diode factor 2, preferably according to the formulas 5a through 5d:

$$j_{D,a}(x_i) = j_{0,1}(x_i) \exp(V_a(x_i)/V_T) + j_{0,2}(x_i) \exp(V_a(x_i)/2/V_T) + V_a(x_i)/R_p(x_i) \quad \text{(Formula 5a)},$$

$$j_{D,b}(x_i) = j_{0,1}(x_i) \exp(V_b(x_i)/V_T) + j_{0,2}(x_i) \exp(V_b(x_i)/2/V_T) + V_b(x_i)/R_p(x_i) \quad \text{(Formula 5b)},$$

$$j_{D,c}(x_i) = j_{0,1}(x_i) \exp(V_c(x_i)/V_T) + j_{0,2}(x_i) \exp(V_c(x_i)/2/V_T) + V_c(x_i)/R_p(x_i) \quad \text{(Formula 5c)},$$

$$j_{D,d}(x_i) = j_{0,1}(x_i) \exp(V_d(x_i)/V_T) + j_{0,2}(x_i) \exp(V_d(x_i)/2/V_T) + V_d(x_i)/R_p(x_i) \quad \text{(Formula 5d)}.$$

In another preferred embodiment of the method according to the invention the voltage images determined in step B are released from other types of measuring defects such that the blurred luminescence images are corrected by sharpness filters (for example Wiener-filter: Norbert Wiener: Extrapolition, Interpolation, and Smoothing of Stationary Time Series, Wiley, N.Y., 1949).

In order to increase the precision of the determined parameters it is advantageous that in step A at least one additional measuring is performed under another measuring condition different from the measuring conditions a and b, and at least one additional voltage-calibrated image is determined accordingly. In step B, this advantageous embodiment therefore shows a superimposed identical system, which is solved in a manner known per se, preferably according to the method of least squares. This leads to higher precision.

The creation and the measurement of the photoluminescence radiation occurs preferably in a manner known per se and is described for example in Würfel, P. et al. "*Diffusions lengths of silicon solar cells from luminescence images*", Journal of Applied Physics, 2007, 101 (123110): p. 1-10 and PCT/AU2007/001050.

In particular, it is advantageous in the method according to the invention to measure the luminescence radiation via a camera, such as a CCD-camera. The measuring signal of the camera is therefore a measure for the intensity of the luminescence radiation. In particular, by using a CCD-camera a spatially resolved measurement of the luminescence radiation can directly occur (by a so-called "mapping"), i.e. no grid-formation or scanning of the surface of the semiconductor structure is necessary.

Impinging the surface of the semiconductor structure to create the photoluminescence radiation occurs preferably with a homogenous intensity with regards to the impinged area of the semiconductor structure. Preferably the semiconductor structure is impinged with a standard spectrum (for example the spectrum AM 1.5), however impingement with other spectra or with monochromatic excitation radiation is also within the scope of the invention, e.g., by creation via a laser. Additionally, it is advantageous to impinge the semiconductor structure with unmodulated light as the excitation radiation.

Furthermore, the scope of the invention includes that the impingement with excitation radiation and the measurement of the luminescence radiation of the semiconductor structure occurs at the same surface of the semiconductor structure. In this case it is essential to add optic filters for the measurement of the luminescence radiation in a manner known per se in order to filter out reflected excitation radiation at the surface of the semiconductor. Additionally, it is within the scope of the invention to perform the impingement with excitation radiation on the one side and the measurement of the luminescence radiation on the other side at two opposite surfaces of the semiconductor structure. In this measurement constellation the semiconductor structure itself acts as a filter in reference to the excitation radiation, so that during the measuring process no interferences occur based on potentially detected excitation radiation.

The measurements of the luminescence radiation are preferably read by a processing unit, such as a computer, and here further processed based to the method according to the invention.

If the external voltage is predetermined in the measuring method according to the invention it is preferably created via a controllable voltage source, which is also connected to the computer for its control.

Advantageously the voltage source that can be controlled additionally comprises a current measuring unit, which under short-circuit conditions measures the current flowing and also forwards the measurements to the computer. This way, in a simple fashion the short-circuit current density can be determined under the respectively given measuring conditions.

The invention claimed is:

1. A method for measuring a semiconductor structure, which comprises an emitter and a base; wherein the semiconductor is a solar cell or a precursor of a solar cell, the method comprising the following steps:

(A) creating luminescence radiation by a planar impingement of the semiconductor structure with an excitation radiation on the semiconductor structure and spatially resolved measurements of the luminescence radiation emitted by the semiconductor structure, with a first measurement being performed, via a camera, at a first measuring condition (a) and depending at least on the measurements yielded from the first measurement, generating a first spatially resolved, voltage-calibrated image $V_a(x_i)$ for a multitude of spatial points $x_i$ of the solar cell from the measurements yielded in step A, and (B) using a processing unit to determine spatially resolved features of the semiconductor structure with regards to at least one of a spatially resolved dark saturation current $j_0(x_i)$, a spatially resolved resistance of an emitter layer $\rho(x_i)$, or a spatially resolved local series resistance $R_s(x_i)$ for the multitude of spatial points $x_i$ dependent at least on the first voltage-calibrated image $V_a(x_i)$ determined in step A, and additionally performing in step A, at least a second measurement at a second measurement condition (b) different from the first measurement condition (a) and, depending at least on the measurements yielded from the second measurement, generating a second spatially resolved, voltage calibrated image $V_b(xi)$ for the multitude of spatial points xi from the measurements yielded in step A such that in step A in the two measurements the first and second measuring conditions (a and b) of the first and second measurements are different with regards to at least one of intensities, spectral compositions of the excitation radiation, or a predetermined external voltage $V_{ext}$, by which the semiconductor structure is impinged via electric contacts, and additionally for each of the first and second measuring conditions and b) a voltage-independent, spatially independent short-circuit current density ($j_{P,a}$, $j_{P,b}$) of the current flowing under the respective measuring conditions with given short-circuit conditions is at least one of predetermined or measured, and in step B determination of the spatially resolved, electric features occurring at each of the spatial locations $x_i$ is dependent on at least the short-circuit current densities ($j_{P,a}$, $j_{P,b}$), and a voltage-dependent, spatially dependent dark current density ($j_{D,a}(x_i)$, $j_{P,b}(x_i)$) for each measurement condition occurs, with the dark current densities ($j_{D,a}(x_i)$, $j_{P,b}(x_i)$) at least being dependent on the voltage-independent dark saturation current density ($j_0,(x_i)$) and the two voltages ($V_a(x_i)$, $V_b(x_i)$) resulting from the respective voltage images for the location $x_i$, without relying on given values for at least one of: dark saturation current density; the resistance of the emitter layer; or the series resistance as external input.

2. The method according to claim 1, wherein in step B the determination of the spatially resolved electric features at each of the spatial points Xi occurs additionally dependent on external voltages (Vext,a) under the first measurement condition (a) and (Vext,b) under the second measurement condition (b), with in step A the semiconductor structure being electrically contacted in both measurements and via the electric contacting the external voltage (Vext,a) is predetermined at the measurement condition and the external voltage (Vext.b) at the second measurement condition (b), or for the voltage (Vext,a) the voltage of the spatial point is predetermined with a lowest voltage in the voltage image (Va(Xi)):

(Vext,a)=(Min(Va(xi))) for all of the spatial points (xi) and according to (Vext,b)=(Min(Vb(Xi))) for all of the spatial points (xi).

3. The method according to claim 2, wherein in step B for each of the spatial points $x_i$ the determination of the spatially resolved electric features occurs such that an equation system is solved, which comprises for each of the two voltage images $V_a(x_i)$ and $V_b(x_i)$ one equation ($G_a$ and $G_b$) each, with the equation $G_a$ comprising at least a spatially resolved, voltage-independent local series resistance $R_s(x_i)$, the voltage $V_a(x_i)$, the external voltage $V_{ext,a}$, the short-circuit current density $j_{P,a}$, and the dark current density $j_{P,a}(x_i)$ and accordingly $G_b$ comprising at least $R_s(x_i)$, $V_b(x_i)$, $V_{ext,b}$, $j_{P,b}$, and $j_{P,b}(x_i)$, and that via the equation system at least one of $R_s(x_i)$ or $j_0(x_i)$ is determined.

4. The method according to claim 3, wherein the equation $G_a$ has a structure according to the formula 1a:

$$R_s(x_i) = \frac{V_{ext,a} - V_a(x_i)}{j_{P,a} + j_{D,a}(x_i)}, \qquad \text{(Formula 1a)}$$

and $G_b$ has a structure according to the formula 1b:

$$R_s(x_i) = \frac{V_{ext,b} - V_b(x_i)}{j_{P,b} + j_{D,b}(x_i)}, . \qquad \text{(Formula 1b)}$$

5. The method according to claim 2, wherein in step A under the first measurement condition (a) an illumination intensity and a spectrum of the excitation radiation are essentially identical to the ones under the second measuring condition (b), however under the first measuring condition (a) an external voltage Vext,a is predetermined, which is different from the external voltage Vext,b predetermined for the second measuring condition (b).

6. The method according to claim 3, wherein in step A at least one additional measurement is performed under measurement conditions different from the first and second measurement conditions (a and b) and at least one additional voltage-calibrated image is determined and in step B wherein a superimposed equation system is solved according to a least square method.

7. The method according to claim 1, wherein in step B for each of the spatial points $x_i$ the determination of the spatially resolved electric features occurs such that an equation system is solved, which for each of the two voltage images $V_a(x_i)$ and $V_b(x_i)$ comprises an equation ($G_{a'}$) and $G_{b'}$, with the equation $G_{a'}$ comprising at least a spatially resolved, voltage independent resistance of the emitter layer $\rho(x_i)$, the voltage $V_a(x_i)$, the short-circuit current density $j_{P,a}$, and the dark current density $j_{D,a}(x_i)$ and accordingly $G_{b'}$ comprising at least $\rho(x_i)$, $V_b(x_i)$, $j_{P,b}$, and $j_{P,b}(x_i)$, and that via the equation system at least one of $\rho(x_i)$ or $j_0(x_i)$ are determined.

8. The method according to claim 7, wherein the equation $G_{a'}$ comprises a structure according to the formula 2a:

$$\nabla^2 V_a(x_i) = \rho(x_i)(j_{P,a} + j_{D,a}(x_i)) \qquad \text{(Formula 2a)}$$

and the equation $G_{b'}$ comprises a structure according to the formula 2b:

$$\nabla^2 V_b(x_i) = \rho(x_i)(j_{P,b} + j_{D,b}(x_i)) \qquad \text{(Formula 2b)}.$$

9. The method according to claim 8, wherein a noise in the measurement data is prevented such that a dual derivation of a Laplace-operator in the formulas 2a and 2b is replaced by a derivation of a polynomial, which is determined via a mathematic filter method, or by the Marr-Hildreth operator being applied to the image.

10. The method according to claim 8, wherein additionally for each of the spatial points $x_i$ and for each of the first and second measuring conditions (a and b) an implicit open circuit voltage (Vimpl.a, Vimpl,b) is determined and the voltage calibrated images Va(Xi) and Vb(Xi) additionally being determined based on the implicit open circuit voltages.

11. The method according to claim 1, wherein the semiconductor structure comprises the solar cell or the precursor of the solar cell and in step A the first measuring condition (a) is selected such that via the electric contacting a current flows ranging from 15% to 35% of a short-circuit current of the solar cell under standard conditions and the second measurement condition (b) is selected such that via the electric contacting a current flows ranging from 65% to 85% of the short-circuit current of the solar cell under standard conditions.

12. The method according to claim 1, wherein the dark current density ($j_{D,a}(x_i)$, $j_{D,b}(x_i)$) or at least one one-diode model is described according to the formulas 3a and 3b, where $V_T$ represents thermal voltage:

$$j_{D,a}(x_i) = j_0(x_i)\exp(V_a(x_i)/V_T) \qquad \text{(Formula 3a)},$$

$$j_{D,b}(x_i) = j_0(x_i)\exp(V_b(x_i)/V_T) \qquad \text{(Formula 3b)}.$$

13. The method according to claim 1, wherein in step A additionally another measurement is performed under a third measuring condition (c), different from the first and second measurement conditions (a and b), and another voltage image Vc(Xi) is determined, the dark current density further described based on an additional parameter and in step B wherein the determination of the spatially resolved features of the semiconductor structure occurs depending on at least the three voltage images, and the dark current densities are additionally described by a voltage-independent local parallel resistance $R_P(x_i)$ according to the formulas 4a through 4c, where $V_T$ represents thermal voltage:

$$j_{D,a}(x_i) = j_0(x_i)\exp(V_a(x_i)/V_T) + V_a(x_i)/R_p(x_i), \qquad \text{(Formula 4a)}$$

$$j_{D,b}(x_i) = j_0(x_i)\exp(V_b(x_i)/V_T) + V_b(x_i)/R_p(x_i), \qquad \text{(Formula 4b)}$$

$$j_{D,c}(x_i) = j_0(x_i)\exp(V_c(x_i)/V_T) + V_c(x_i)/R_p(x_i), \qquad \text{(Formula 4c)}.$$

14. The method according to claim 13, wherein in step A additionally another measurement is performed under measuring condition (d), different from the first, second and third measuring conditions (a, b and c), and in step A another voltage image $V_d(Xi)$ is determined such that the dark current densities additionally are described based on another parameter, and in a step B a determination of the spatially resolved features of the semiconductor structure occurs depending on at least one of the four voltage images, wherein the dark current density is additionally described by a second diode-dependency with a diode factor according to the formulas 5a through 5d, where $V_T$ represents thermal voltage:

$$j_{D,a}(x_i) = j_{0,1}(x_i)\exp(V_a(x_i)/V_T) + j_{0,2}(x_i)\exp(V_a(x_i)/2/V_T) + V_a(x_i)/R_p(x_i) \qquad \text{(Formula 5a)},$$

$$j_{D,b}(x_i) = j_{0,1}(x_i)\exp(V_b(x_i)/V_T) + j_{0,2}(x_i)\exp(V_b(x_i)/2/V_T) + V_b(x_i)/R_p(x_i) \qquad \text{(Formula 5b)},$$

$$j_{D,c}(x_i) = j_{0,1}(x_i)\exp(V_c(x_i)/V_T) + j_{0,2}(x_i)\exp(V_c(x_i)/2/V_T) + V_c(x_i)/R_p(x_i) \qquad \text{(Formula 5c)},$$

$$j_{D,d}(x_i) = j_{0,1}(x_i)\exp(V_d(x_i)/V_T) + j_{0,2}(x_i)\exp(V_d(x_i)/2/V_T) + V_d(x_i)/R_p(x_i) \qquad \text{(Formula 5d)}.$$

15. The method according to claim 1, wherein the voltage images determined in step A are released from measurement noise and other measurement defects such that blurred luminescence images are corrected by sharpness filters.

* * * * *